United States Patent [19]

Ta et al.

[11] Patent Number: 5,891,119

[45] Date of Patent: Apr. 6, 1999

[54] ABSORPTIVE ARTICLE

[75] Inventors: Kouki Ta, Shiga-ken; Seiji Yokota, Moriyama, both of Japan

[73] Assignee: Chisso Corporation, Osaka, Japan

[21] Appl. No.: 721,941

[22] Filed: Sep. 27, 1996

Related U.S. Application Data

[63] Continuation of Ser. No. 271,765, Jul. 7, 1994, abandoned.

[30] Foreign Application Priority Data

Jul. 8, 1993 [JP] Japan ................................ 5-193993

[51] Int. Cl.$^6$ .................................................. A61F 13/15
[52] U.S. Cl. ........................... 604/378; 604/365; 604/367
[58] Field of Search ................................ 604/365, 366, 604/368, 378, 385.1

[56] References Cited

U.S. PATENT DOCUMENTS

| | | | |
|---|---|---|---|
| 4,655,757 | 4/1987 | McFarland et al. | 604/366 |
| 4,851,284 | 7/1989 | Yamanoi et al. | 428/284 |
| 5,019,063 | 5/1991 | Marsan et al. | 604/368 |
| 5,188,624 | 2/1993 | Young, Sr. et al. | 604/366 |
| 5,302,447 | 4/1994 | Ogata et al. | 428/288 |
| 5,304,161 | 4/1994 | Noel et al. | 604/378 |
| 5,350,370 | 9/1994 | Jackson et al. | 604/366 |
| 5,356,403 | 10/1994 | Faulks et al. | 604/368 |
| 5,360,420 | 11/1994 | Cook et al. | 604/368 |
| 5,486,167 | 1/1996 | Dragoo et al. | 604/368 |

FOREIGN PATENT DOCUMENTS

| | | |
|---|---|---|
| 317058 | 5/1989 | European Pat. Off. . |
| 2-074254 | 3/1990 | Japan . |
| WO 90/04376 | 5/1990 | WIPO . |
| WO 93/21881 | 11/1993 | WIPO . |

*Primary Examiner*—John G. Weiss
*Assistant Examiner*—David J. Cho
*Attorney, Agent, or Firm*—Fay, Sharpe, Beall, Fagan, Minnich & McKee

[57] ABSTRACT

An absorptive article having a superior liquid-absorptivity, without returning of the absorbed body fluid and being compact is provided.

which article comprises a liquid-permeable front sheet, a liquid-impermeable back sheet and an absorbent placed between the above two sheets, this absorbent being composed of at least two layers. As those used in the first layer and the second layer in Examples 1 to 3 were mixed to obtain homogeneous absorbents.

The preparation conditions, the quantity of liquid absorbed, the percentage of absorbed liquid and the tensile strength after dried, these absorbers are shown in Tables 1 and 2.

6 Claims, No Drawings

ABSORPTIVE ARTICLE

This is a continuation of U.S. application Ser. No. 08/271,765, filed Jul. 7, 1994, now abandoned.

BACKGROUND OF THE INVENTION

1. Field of the Invention

This invention relates to an absorptive article used for napkin for menstruation, pad for mother's milk, pad for incontinence of urine, throwaway diaper, pad for puerperium, etc. More particularly, it relates to an absorptive article having a superior liquid-absorptivity making the best use of the liquid-absorptivity of highly water-absorptive polymers and in which the body fluid once absorbed does not return, and is also compact in its structure.

2. Description of the Related Art

As absorptive articles using hotmelt-adhesive fibers, mixtures of hydrophilic fibers, hotmelt-adhesive synthetic crimped fibers and highly water-absorptive polymers have been known (Japanese patent application laid-open No. Hei 2-74254).

Further, Japanese Utility Model publication No. Sho 56-6098 discloses that an absorptive material composed of pulp fibers, gel-forming substance particles and filaments, can absorb a large quantity of water and the absorbed water does not return easily.

However, in the above known absorptive articles, highly water-absorptive polymers have been used in admixture in order to increase the water-absorbing force of pulp fibers or the like, but there have been raised such problems that the liquid-absorptive properties of the pulp fibers in the absorptive article are so directional that the absorption is carried out in spots, and since the absorbed liquid is not efficiently diffused into the highly water-absorptive polymers, the water-absorptivity of the polymers cannot be sufficiently effected. Thus, the highly water-absorptive polymers have to be used in a quantity exceeding a necessary one therefor.

Further, it is required for the absorptive articles that the liquid absorbed therein should not return to the surface thereof. Since the liquid-absorptivity of the highly water-absorptive polymers is not sufficiently effected as described above, there has been raised such a problem that although a large quantity of the highly water-absorptive polymer is used, it is impossible to satisfy the above requirement.

SUMMARY OF THE INVENTION

The present inventors have made extensive research in order to solve the above-mentioned problem, and so a result have complete the present invention.

The present invention resides in the following aspects.
(1) An absorptive article comprising a liquid-permeable front sheet, a liquid-impermeable back sheet and an absorbent placed between the above two sheets, the absorbent being composed of at least two layers, a first layer thereof being placed close to the front sheet and composed of hydrophilic fibers and hotmelt-adhesive fibers, and a second layer thereof being placed close to the back sheet and composed of a highly water-absorptive polymer and hotmelt-adhesive fibers.
(2) An absorptive article according to item (1), wherein the first layer is a mixture of 20 to 90% by weight of hydrophilic fibers and 10 to 80% by weight of hotmelt-adhesive fibers, and the second layer is a mixture of 50 to 80% by weight of a highly water-absorptive polymer and 20 to 50% by weight of hotmelt-adhesive fibers.
(3) An absorptive article according to item (1) or (2), wherein the hotmelt-adhesive fibers are conjugate fibers of two components having different melting points and a conjugate ratio of 30/70 to 70/30.
(4) An absorptive article according to item (3), wherein the basis weight of the first layer is in the range of 20 to 300 $g/m^2$ and the basis weight of the second layer is in the range of 50 to 500 $g/m^2$.
(5) An absorptive article according to item (1) or (2), wherein the liquid permeable front sheet is a polyolefin non-woven fabric having a basis weight in the range of 25 to 35 $g/m^2$ and said back sheet is a polyethylene sheet.
(6) An absorptive article according to item (1) to (2), wherein the highly water-absorptive polymer is one capable of absorbing water in a quantity of 30 times or more its weight.
(7) An absorptive article according to item (1) or (2), wherein the hydrophilic fibers are pulp.

DETAILED DESCRIPTION OF PREFERRED EMBODIMENTS

In the present invention, as the liquid-permeable front sheet, polyolefin non-woven fabrics having a basis weight of 25 to 35 $g/m^2$, are usable, and as the liquid-impermeable back sheet, known materials such as polyethylene film or the like are usable.

Examples of hydrophilic fibers used as the absorbent in the present invention are natural fibers such as pulp, cotton, wool, etc. and semisynthetic fibers such as rayon, acetate fibers, etc., and among them, pulp, cotton and rayon are preferable. Pulp is classified into mechanical pulp, chemical pulp, semichemical pulp, etc., depending upon its production process, and among these, chemical pulp is preferable. Particularly preferable chemical pulp is fluff pulp obtained by fibrillating wound-up pulp composed of Kraft pulp.

The highly water-absorptive polymer used in the present invention refers to a polymer which can absorb water in a quantity of 30 times or more its self weight. For example, saponified starch polyacrylonitrile-grafted polymer, starch polyacrylate-grafted polymer, cross-linked or graft-polymerized cellulose, saponified acrylic acid polymer, saponified acrylic acid copolymer, saponified polyethylene oxide, carboxymethylcellulose, etc. are usable.

In the absorptive article of the present invention, a product obtained by subjecting mixed fibers of 20 to 90% by weight of hydrophilic fibers with 10 to 80% by weight of hotmelt-adhesive fibers to hotmelt-adhesion treatment is preferably used as the first layer of the absorbent. If the weight of the hotmelt-adhesive fibers is less than 10% by weight, the tenacity of the absorbent after hotmelt-adhesion is insufficient and at the same time, the retention of the hydrophilic fibers due to matrix structure formed by hotmelt-adhesive fibers is insufficient Further, if the weight of the hydrophilic fibers is less than 20% by weight, prevention of leakage of the highly water-absorptive polymer swelled at the time of absorption of the body fluid, onto the surface layer is insufficient.

The matrix structure referred to herein means a sterically reticular structure. For example, as to this matrix structure, when cellulose is mixed with hotmelt-adhesive fibers, then the mixture is subjected to heat treatment for hotmelt-adhering the hotmelt adhesive fibers, and the resulting material is dissolved in 70% sulfuric acid solution and remove the resulting hydrophilic fibers, it can be easily observed that the matrix structure is formed by the hotmelt-adhesive fibers.

Further, as the second layer of the absorbent in the present invention, a product obtained by subjecting a mixture of 50 to 80% by weight (preferably 60 to 70% by weight) of a highly water-absorptive polymer with 20 to 50% by weight (preferably 30 to 40% by weight) of hotmelt-adhesive fibers, to hotmelt-adhesion is used. If the quantity of the hotmelt-adhesive fibers is less than 20% by weight, the tenacity after hotmelt-adhesion is insufficient, and the retention of the highly water-absorptive polymer interior of matrix consisting of hotmelt-adhesive fibers is insufficient. Further, if the weight of the highly water-absorptive polymer is less than 50% by weight, the absorption of the body fluid is insufficient.

Further, if necessary, as a third layer having the same composition as the above first layer, or a non woven fabric consisting of hotmelt-adhesive fibers alone, or consisting of mixed fibers of hydrophilic fibers with hotmelt-adhesive fibers may be laminated under the second layer unless the effect of the present invention is not hindered.

Examples of a resin forming the hotmelt-adhesive fibers used for the absorptive article of the present invention are thermoplastic resins such as polyamides, polyesters, low melting copolymerized polyesters, polyvinyl acetate, polystyrene, polyurethane elastomer, polyester elastomer, polypropylene, high density polyethylene, low density polyethylene, linear low density polyethylene, copolymerized polypropylene, copolymerized polyethylene, etc. In order to prevent degradation of hydrophilic fibers and highly water-absorptive polymers, the heat-treatment temperature is preferred to be not so high. Thus, thermoplastic resins having a melting point of 60° to 200° C. are preferred.

The hotmelt-adhesive fibers are preferred to be conjugate fibers of two components having different melting points. The conjugate type may be either of side by side type or sheath-and-core type whose sheath component is a lower melting point component, and also may be a material wherein at least one conjugate component forms at least one portion of the fiber surface. The conjugate ratio is within a range of 30/70 to 70/30, preferably 40/60 to 60/40, more preferably 45/55 to 55/45. If the conjugate ratio of the hotmelt-adhesive component (lower melting point component) of the hotmelt-adhesive fibers is less than 30%, the hotmelt-adhesion is insufficient, and a sufficient tenacity for the adsorptive article is not obtained. Further, if the ratio exceeds 70%, the quantity of the melted component at the adhered point of the fibers to one another at the time of the hotmelt-adhesion increases; hence the melted part is liable to become an obstacle hindering the diffusion of the body fluid.

The hotmelt-adhesive fibers used for the absorptive article of the present invention are preferred to be crimped ones. The crimped shape includes a two-dimensional one obtained by affording mechanical crimps, a three-dimensional one having developed a latent crimpability due to the difference in the heat shrinking properties between the components of conjugate fibers, etc. These crimped shapes may be employed alone or in admixture. As the crimped fibers used in the present invention, those having three-dimensional crimps having developed a latent crimpability are particularly preferred due to their superior bulky performance. The number or crimps is 4 to 30 crimps per inch, preferably 8 to 20 crimps per inch.

By using crimped fibers, it is possible to form a far more bulky matrix of crimped fibers, than the matrix of non-crimped fibers. This bulky matrix has a high void ratio i.e. many voids; hence it has a large passageway of the body fluid. Thus, the matrix using crimped fibers has a superior permeability of the body fluid. Particularly when three-dimensional crimped fibers are used for the first layer, the water-permeable effect is large. The first layer is a blend of hydrophilic fibers with crimped fibers, and cellulose is uniformly arranged in the bulky matrix formed by crimped fibers; hence the distance between adjacent hydrophilic fibers is longer as compared with that in the matrix formed by non-crimped fibers, and the hydrophilic fibers are filled suitably to retain gaps. Further, the second layer is a blend of a highly water-absorptive polymer with crimped fibers, and the highly water-absorptive polymer is uniformly arranged in the bulky matrix formed by crimped fibers, and the distance between adjacent, highly water-absorptive polymers is longer than that in the matrix formed by non-crimped fibers, and the highly water-absorptive polymers are filled suitably to retain the gaps.

The physical properties of the absorptive article of the present invention are much influenced by the denier and the cut length of the hotmelt-adhesive fibers. The hotmelt-adhesive fibers in the first layer and the second layer of the absorbent are preferred to have 1 to 50 denier (preferably 2 to 40 denier) and a cut length of 3 to 100 mm (preferably 5 to 80 mm). If the denier is less than 1 deniers, the bulkiness is insufficient, and if it exceeds 50 deniers, it is difficult to form the matrix structure. On the other hand, if the cut length is less than 3 mm, it is difficult to form the matrix structure, and if it exceeds 100 mm, the dispersion of the hotmelt-adhesive fibers is inferior, the retention of the cellulose of the highly water-absorptive polymer is insufficient, so that the cellulose or the highly water-absorptive polymer slips off.

The respective layers of the absorbent used in the present invention are obtained by mixing the above-mentioned suitable quantity of the hydrophilic fibers or the highly water-absorptive polymer with the hotmelt-adhesive fibers, when the hotmelt-adhesive fibers are made to a web according to carding process or dry pulp process (aid-laid process), and subjecting the web to heat-treatment. By laminating the first layer and the second layer separately prepared in advance and again heat-treating, it is possible to hotmelt-adhere the two layers. Further, there is another process wherein, while a web for the first layer and a web for the second layer are simultaneously prepared, they are heat-treated by means or the same heat-treating device to obtain a laminated absorbent.

The first layer of the absorbent is preferred to have a basis weight of 20 to 300 g/m², preferably 50 to 200 g/m². If the basis weight of the first layer is less than 20 g/m², it is difficult to prevent the leakage of body liquid absorbed and swelled in the highly water-absorptive polymer to the surface of the absorptive article at the time of absorption of the body fluid. On the other hand, if the basis exceeds 300 g/m², the layer becomes so bulky that the diffusion and absorption of the body fluid become slow.

The second layer of the absorbent is preferred to have a weight of 50 to 500 g/m², preferably 100 to 200 g/m². If the basis weight of the second layer is less than 50 g/m², the quantity of the highly water-absorptive polymer for absorbing the body fluid becomes insufficient. If the basis weight of the second layer exceeds 500 g/m², the highly water-absorptive polymer swells at the time of absorbing the body fluid; hence deformation of the absorptive article is liable to occur.

The absorptive article of the present invention is obtained by intervening the above-mentioned laminated absorbent between the liquid-permeable front sheet and the liquid-impermeable back sheet.

The absorptive article of the present invention is characterized in that by using the absorbent whose hotmelt-adhesive fibers have formed a matrix structure by heat-treatment, the collapse of a bulkiness of the article is prevented to afford a good and resistant water-permeability. By forming the matrix structure in the hotmelt-adhesive fibers, even when the hydrophilic fibers in the first layer cause collapse of the bulkiness at the time of absorption of the body fluid, a decrease of the bulkiness of the first layer can be prevented. Thus, the passageway of the body fluid into the highly water-absorptive polymer can be secured, thereby the permeability of the body fluid does not decrease. Further, the body fluid permeated into the second layer passes through the gaps of the matrix of the second layer, diffuses into the highly water-absorptive polymer having not yet absorbed water and is absorbed therein.

The absorptive article of the present invention is characterized in that, by forming the matrix structure of the hotmelt-adhesive fibers, the article is provided with a superior moldability and an adequate flexibility. The moldability herein means that the absorptive article is faithfully molded in a mold frame so as to fit the body, and there is no feeling of incompatibility at the time of its fitting to a human body. Further, the adequate flexibility referred to herein means that the article can be stored by compaction, and when it is used, the original volume is readily recovered, and there is no stiff feeling.

The absorptive article of the present invention is further characterized in that the first layer and the second layer of the absorbent are melt-adhered to be integrated. Due to the integration, the first layer and the second layer causes neither deviation nor shift, and further, it is possible to reduce the quantity of the hydrophilic fibers; hence it is possible to produce an absorptive article which is not too bulky, has no malaise at the time of its fitting and is compact. Due to its compactness, the transportation cost and the storage cost can be not only reduced, but also it is superior in the portable properties.

EXAMPLE

The present invention will be described in more detail by way of Examples and Comparative examples. In addition, the quantity of water absorbed, the percentage of absorbed water, the percentage of absorbed water and the tensile strength in dry state were measured and calculated as follows:

Quantity of water absorbed

In order to evaluate the returning of the absorbed body fluid, the quantity of fluid absorbed and not returned was measured.

The dry weight of a sample (absorbent) (400 g/m$^2$) was measured. Then, an artificial urine (20 ml) colored with red ink was dropped by means of a transfer pippet, from a height of 1 cm onto a central part of the sample. After one minute, the sample having absorbed the liquid was moved onto a water-absorbing material mentioned below, followed by placing a load of 34 g/cm$^2$ over the whole surface of the sample, allowing it to stand for one minute, removing the load and measuring the weight of the sample having absorbed the liquid. The value obtained by substracting the dry weight of the sample from the weight of the sample having absorbed the liquid was made the quantity of the liquid absorbed (n=3). As the water-absorbing material, there was used a material obtained by wrapping a water-absorbing layer (basis weight: 280 g/m$^2$) consisting of a cotton pulp (90% by weight) and a highly water-absorbing polymer (10% by weight) uniformly dispersed therein, covered with one layer of a tissue paper (basis weight: 18 g/m$^2$).

Percentage of absorbed liquid

The value calculated by the following equation was made the percentage of absorbed liquid (%):

(Quantity of liquid absorbed÷20 g)×100=percentage of absorbed liquid (%)

Content of percentage of absorbed liquid

The percentage of existence of absorbed liquid was calculated by the following equation, and the percentage of absorbed liquid was separately expressed as regards the first layer and the second layer:

(Quantity of liquid absorbed in the first layer÷total quantity of liquid absorbed)×100=percentage of absorbed liquid in first layer (%)

(Quantity of liquid absorbed in the second layer÷total quantity of liquid absorbed)×100=percentage of absorbed liquid in second layer (%)

Tensile strength of dry state

Sample (the absorbent: basis weight 400 g/m$^2$) was cut into 5×15 cm rectangle, and its tensile strength was measured by means of a tensile tester under conditions of a test length of 100 mm and a rate of drawing of 100 mm/min. (n=3).

The following various kinds of raw materials were used (composition ratio being all based on % by weight, and hereinafter abbreviated to %):

Conjugate fiber-1: 10 d×15 mm (fiber denier×fiber length) hotmelt-adhesive fiber composing of polypropylene/polyethylene (=50%/50%) sheath and core type conjugate fiber having no crimp.

Conjugate fiber-2: 10 d×15 mm hotmelt-adhesive fiber composing of polypropylene/polyethylene (=50%/50%) side by side type conjugate fiber having two-dimensional crimps (number of crimps: 13 crimps/inch).

Conjugate fiber-3: 10 d×15 mm hotmelt-adhesive fiber composing of polypropylene/polyethylene (=50%/50%) side by side type conjugate fiber having three-dimensional crimps (number of crimps: 8 crimps/inch).

Pulp: fluff pulp

Highly water-absorptive polymer: Aqualic CA W-4 cross-linked sodium acrylic acid polymer (trademark of product made by Nippon Shokubai Co., Ltd)

Preparation conditions of the absorbing materials in the respective Examples and Comparative examples are as follows:

(EXAMPLES 1 to 3)

Raw materials of the first layer of an absorbent in a necessary quantity weighted and taken are roughly dispersed by means of a mixer, followed by air-feeding the roughly dispersed raw materials in a similar manner to dry pulp process to fallen in dispersion state, and sucking it by means of a vacuum cleaner to collect it on cheese-cloth of 25 meshes to form the first layer. Next, the raw materials of the second layer are similarly processed and collected to form the second layer.

Next, the first layer and the second layer are lapped together and heat-treated by means of a suction band dryer, under heat-treatment conditions (temperature: 150° C., time: 10 seconds and air feeding rate: 1.9 m/sec.), followed by taking out the sample from the suction band dryer, just thereafter placing a load of 17 g/cm$^2$ on it and removing the load after one minute, to obtain an absorbent for the present invention.

The preparation conditions, the quantity of liquid absorbed, the percentage of absorbed liquid, the content of the percentage of absorbed liquid and the tensile strength dry state, of these absorbents are shown in Tables 1 and 2.

(COMPARATIVE EXAMPLES 1 and 2)

Various kinds of absorbing materials were obtained under the same conditions as in Example 1 except that the same kinds and equal quantities of raw materials as those used in the first layer and the second layer in Examples 1 to 3 were mixed to obtain homogeneous single layer absorbents.

The preparation conditions, the quantity of liquid absorbed, the percentage of absorbed liquid and the tensile strength after dried of these absorbents are shown in Tables 1 and 2.

TABLE 1

| | Composition ratio (% by weight) | | | | |
|---|---|---|---|---|---|
| | First layer | | Second layer | | |
| Examples | Hotmelt-adhesive fibers | Hydro-philic fibers | Hotmelt-adhesive fibers | | Highly water-absorptive polymer |
| Example 1 | Conjugate-1 20 | 80 | Conjugate-1 | 40 | 60 |
| Example 2 | Conjugate-2 20 | 80 | Conjugate-2 | 40 | 60 |
| Example 3 | Conjugate-3 20 | 80 | Conjugate-3 | 40 | 60 |
| | Single layer | | | | |
| Comparative examples | Hotmelt-adhesive fibers | | Hydrophilic fibers | | Highly water-absorptive polymer |
| Comp. ex. 1 | Conjugate-2 30 | | 40 | | 30 |
| Comp. ex. 2 | Conjugate-3 30 | | 40 | | 30 |

Note 1: First layer/second layer = 50/50

TABLE 2

| Examples and Comparative examples | Amount of liquid absorbed (g) | Percentage of absorbed liquid (%) | Content of percentage of absorbed liquid (%) | | Tensile strength after drying (g/5 cm) |
|---|---|---|---|---|---|
| | | | First layer | Second layer | |
| Example 1 | 13.12 | 66.1 | 32.4 | 67.6 | 1926 |
| Example 2 | 14.51 | 72.6 | 24.6 | 75.4 | 1671 |
| Example 3 | 13.48 | 67.4 | 17.3 | 82.7 | 1738 |
| Compar. ex. 1 | 7.17 | 35.9 | — | — | 644 |
| Compar. ex. 2 | 5.56 | 27.8 | — | — | 309 |

Note 1: The tensile strength after dried refers to a value calculated into 400 g/m$^2$.

In examples 1 to 3 wherein hotmelt-adhesive fibers and pulp was arranged in the first layer and hotmelt-adhesive fibers and a highly water-adsorptive polymer was arranged in the second layer, the percentage of absorbed liquid amounted to about 70%, whereas in Comparative examples 1 and 2 wherein hotmelt-adhesive fibers, pulp and highly water-absorptive polymer were homogeneously mixed, the percentage of absorbed liquid amounted only to about 30%.

As the reason for the above, it is considered that there is a large difference between the liquid-absorbing behaviors of pulp and highly water-absorptive polymer. In the case of no load, pulp and highly water-absorptive polymer, both absorb liquid, whereas in the case where a load has been applied, pulp returns the absorbed liquid, whereas the highly liquid-absorptive polymer does not return the liquid absorbed therein.

Further, in the case of Examples 1 to 3, the body fluid having entered into the first layer is absorbed only by pulp, permeated through the first layer and led into the second layers without any diffusion. Since the diffusion in the first layer is small, the quantity absorbed by pulp which is liable to return the body fluid is enough to be small. In the second layer, the body fluid entered thereinto is more broadly diffused along with hotmelt-adhesive fibers and is absorbed by highly water-absorptive polymer. The body fluid absorbed by the highly water-absorptive polymer does not return even when a load has been applied.

Whereas, in the case of Comparative examples 1 and 2 wherein hotmelt-adhesive fibers, pulp and a highly water-absorptive polymer have been homogeneously dispersed, the body fluid having entered in a similar manner as in Examples 1 to 3 is absorbed by the highly water-absorptive polymer on the surface, during permeating from the surface and diffusing onto the back surface; hence the moving speed into the inside is so slow that the body fluid is retained only at a part close to the surface. Accordingly, the quantity of the body fluid absorbed by pulp, but going backward, when a load has been applied, is larger than that in the case of Examples 1 to 3. Further, the quantity of the liquid absorbed by the inside highly water-absorptive polymer is less by the quantity in which the diffusion of the body fluid does not advance. This means that the highly water-absorptive polymer has not been effectively utilized, as compared with the case of Examples 1 to 3.

In short, in Examples 1 to 3, the quantity of liquid absorbed by pulp is less than that in Comparative examples 1 and 2, and the quantity of liquid absorbed by the highly water-absorptive polymer is larger than that in Comparative examples 1 and 2. Thus, in the case of Comparative examples 1 and 2 wherein the quantity of liquid absorbed by the highly water-absorptive polymer which causes no liquid return even when a load has been applied, is small, the quantity of liquid absorbed is less.

Further, the differences among fibers of no crimp, two-dimensional crimped fibers and three-dimensional crimped fibers in Examples 1 to 3 were discussed as follows.

The percentage of absorbed liquid in the second layer in the case of Example 2 using two-dimensional crimped fibers was higher than that in the case of Example 1 using fibers of no crimp, and the percentage in the case of Example 3 using three-dimensional crimped fibers was still higher. Thus, it has been confirmed that as to the speed of the body fluid passing through the first layer, and speed in the case using two-dimensional crimped fibers was faster than that in the case using fibers of no crimp, and further that in the case using three-dimensional crimped fibers was faster than that in the case using two-mentional crimped fibers.

Effectiveness of the Invention

As compared with conventional absorptive articles, wherein a highly water-absorptive polymer, hydrophilic fibers and hotmelt-adhesive fibers have been homogeneously dispersed, in the case of the absorptive article of the present invention, hydrophilic fibers and a highly water-absorptive polymer were respectively separated in the first layer and the second layer and further they were combined with hotmelt-adhesive fibers, whereby not only the spot-like liquid-absorptivity of the hydrophilic fibers was excluded, but also a matrix structure due to hotmelt-adhesive fibers was formed, thereby the body fluid could be broadly diffused over the whole of the absorptive article. Thus, the water-absorptivity of the highly water-absorptive polymer could be fully effected, and at the same time with the improvement in the liquid absorptivity, the return of the absorbed body fluid could be prevented.

Further, since the liquid-absorptivity has been improved, the quantity of the hydrophilic fibers required could be reduced, and the absorptive article which had so far been bulky due to the hydrophilic fibers could be thinly prepared, that is, a compact absorptive article could be prepared. And yet, since hotmelt-adhesive fibers were arranged in the first layer and the second layer to form a matrix structure, the simultaneous molding of the two layers at the same time with integration thereof became possible, and further, since the article has an adequate flexibility an absorptive article having no incompatibleness at the time of fitting could be prepared.

What we claim is:

1. An absorptive article comprising a liquid-permeable front sheet, a liquid-impermeable back sheet and an absorbent placed between the above two sheets, said absorbent being composed of at least two layers, a first layer thereof being placed close to said front sheet and composed of 20 to 90% by weight of hydrophilic fibers and 10 to 80% by weight of hotmelt-adhesive fibers, and a second layer thereof being placed close to the back sheet and composed of 50 to 80% by weight of a highly water-absorptive polymer and 20 to 50% by weight of hotmelt-adhesive fibers, said hotmelt-adhesive fibers both in said first layer and said second layer being conjugate fibers of two components having different melting points and a conjugate ratio of 30/70 to 70/30, having a fineness of 2 to 50 denier, a length of 5 to 100 mm and 4 to 30 crimps per inch, and being heat-treated to achieve melt-adherence to one another to form a matrix.

2. An absorptive article according to claim 1, wherein the basis weight of said first layer is in the range of 20 to 300 $g/m^2$ and the basis weight of said second layer is in the range of 50 to 500 $g/m^2$.

3. An absorptive article according to claim 1, wherein said liquid permeable front sheet is a polyolefin non-woven fabric having a basis weight in the range of 25 to 35 $g/m^2$ and said back sheet is a polyethylene sheet.

4. An absorptive article according to claim 1, wherein said highly water-absorptive polymer is one capable of absorbing water in a quantity of 30 times or more its weight.

5. An absorptive article according to claim 1, wherein said hydrophilic fibers are pulp.

6. The article of claim 1, wherein said matrix is a sterically reticular structure.

* * * * *